United States Patent [19]

Rabenecker et al.

[11] Patent Number: 5,312,593
[45] Date of Patent: May 17, 1994

[54] COLORIMETRIC DETECTING DEVICE HAVING A REAGENT SUPPLY VESSEL

[75] Inventors: Horst Rabenecker, Klein Parin; Klaus-Peter Rindt; Stephan Scholtissek, both of Lübeck; Wolfgang Breithaupt, Seedorf, all of Fed. Rep. of Germany

[73] Assignee: Drägerwerk Aktiengesellschaft, Lübeck, Fed. Rep. of Germany

[21] Appl. No.: 70,218

[22] Filed: Jun. 1, 1993

Related U.S. Application Data

[63] Continuation of Ser. No. 746,471, Aug. 16, 1991, abandoned.

[30] Foreign Application Priority Data

Aug. 16, 1990 [DE] Fed. Rep. of Germany ....... 4025842

[51] Int. Cl.$^5$ .................. G01J 1/48; G01N 31/22
[52] U.S. Cl. ..................... 422/86; 422/56; 422/58; 422/61; 422/83; 422/85; 422/102
[58] Field of Search ............ 422/56, 58, 61, 68.1, 422/83–86, 100, 102

[56] References Cited

U.S. PATENT DOCUMENTS

| | | | |
|---|---|---|---|
| 3,022,141 | 2/1962 | Grosskopf | 422/86 |
| 3,689,224 | 9/1972 | Agnew et al. | 422/61 |
| 3,697,227 | 10/1972 | Goldstein et al. | 422/61 |
| 3,937,213 | 2/1976 | McDonald | 422/61 |
| 4,229,813 | 10/1980 | Lilly et al. | 422/56 |
| 4,304,869 | 12/1981 | Dyke | 435/299 |
| 4,329,153 | 5/1982 | Leichnitz | 422/61 |
| 4,769,333 | 9/1988 | Dole et al. | 422/61 |
| 4,813,432 | 3/1989 | Saint Amand | 422/101 |
| 4,857,453 | 8/1989 | Ullman | 422/58 |
| 4,865,813 | 9/1989 | Leon | 422/61 |
| 4,918,025 | 4/1990 | Grenner | 422/102 |
| 4,927,605 | 5/1990 | Dorn et al. | 422/61 |
| 4,943,522 | 7/1990 | Eisenger et al. | 422/57 |
| 4,960,691 | 10/1990 | Gordon et al. | 422/70 |

Primary Examiner—James C. Housel
Assistant Examiner—Jan M. Ludlow
Attorney, Agent, or Firm—Walter Ottesen

[57] ABSTRACT

A detecting device in the form of a testing tube or dosimeter having a carrier indicating a color reaction requires a reagent liquid for carrying out a measurement. The reagent liquid is contained in a separate reagent supply vessel and the carrier is impregnated with a color indicator. For carrying out a measurement, the reagent supply from the supply vessel must be brought into contact with the porous carrier. A uniform wetting of the surface of the carrier subjected to the reagent solution is achieved after the reagent solution is emptied from the supply vessel. This is achieved by providing a reagent collection chamber between the carrier and the reagent supply vessel into which the reagent solution pours when the supply vessel is opened and wherein the reagent solution is accommodated and into which the carrier extends so that its end face is subjected to the reagent solution so that this end face can be wetted at the same time.

28 Claims, 2 Drawing Sheets

COLORIMETRIC DETECTING DEVICE HAVING A REAGENT SUPPLY VESSEL

This is a continuation of application Ser. No. 07/746,471, filed Aug. 16, 1991 now abandoned.

FIELD OF THE INVENTION

The invention relates to a colorimetric detecting device for gaseous or liquid test quantities which enter a color-change reaction with a reagent solution applied to a porous carrier containing a color indicator. The detecting device has a housing which makes the carrier visible and a reagent supply vessel whose contents are brought into contact with the carrier such that the carrier is wetted with the reagent solution.

BACKGROUND OF THE INVENTION

U.S. Pat. No. 4,329,153 discloses such a detecting device in the form of a testing tube. This testing tube is provided for detecting and measuring copper aerosols in air. The glass tube is frangible at its tips and a breakable glass ampule and a reaction layer are disposed one behind the other in the through-flow direction of the testing tube. The glass ampule is provided as a reagent supply vessel and the reaction layer of silica gel is provided as a carrier and is impregnated with a color indicator for copper. The ampule is filled with nitric acid and a filter layer is disposed between the ampule and the reaction layer. The filter layer holds back copper aerosols from the test quantity of air when passing the test quantity through the testing tube via suction.

After the sample has been taken, the ampule is broken and care must be taken that the entire contents of the ampule are distributed uniformly over the filter layer containing the copper aerosol as well as over the reaction layer having the color indicator.

The break of the ampule releases the reagent liquid immediately after breaking the ampule because of the way the ampule is mounted in the testing tube with the reagent fluid pouring directly onto the filter layer and the reaction layer before the residual amount is removed from the ampule. For this reason, color reactions take place before a uniform solution of the copper aerosols in the nitric acid and a uniform wetting of the reaction layer take place. This causes color changes to occur at certain locations of the reaction layer wetted with the detecting reagent; however, at other locations which are not yet wetted, the color change occurs only later. The non-uniform color change of the reaction layer resulting therefrom makes a reliable reading or comparison of the degree of color change with a color standard difficult.

In order to bring the entire contents of the ampule together with the test quantity to be investigated and the color reagent for a quantitative conversion, the content of the ampule must be driven out and applied to the reaction surface in a non-reproducible manner, for example, by means of whirling movements of the testing tube held in the hand with the open ampule. In this way, the reliability of the measurement method is essentially dependent upon the expertise of the user to manipulate the detecting device in a suitable manner.

SUMMARY OF THE INVENTION

In view of the foregoing, it is an object of the invention to improve a colorimetric detecting device of the kind described above such that a uniform wetting of the surface of the carrier subjected to the reagent becomes possible after emptying the reagent solution from the supply vessel.

According to a feature of the device of the invention, a reagent collection chamber is provided between the carrier and the reagent supply vessel into which the reagent solution pours when the supply vessel is opened and is caught therein and into which the carrier extends for simultaneously wetting its end face exposed to the reagent.

The invention is for colorimetric detecting devices in a form which can be utilized in through-flow testing tubes or in the form of collecting tubes (dosimeters) open at one end as well as for badge-shaped indicator carriers which must all be soaked with a reagent solution for initiating a color reaction and with which the test quantity to be detected is converted to a reaction product between the test quantity and the reagent with the reaction product making a color reaction possible. In this context, and as to the significance of the invention, water is viewed as a solvent for the reaction components bonded in the carrier in the simplest case and, for the most complex case, an organic or aqueous solution of all required reaction components can be seen as the solvent.

The colorimetric detecting device of the invention is suitable for permitting the detecting reactions to take place for the known testing tube detection in an especially advantageous manner. For example, for detecting copper aerosols, the reagent supply vessel is filled with nitric acid and the carrier made of silica gel is impregnated with a color reagent for copper, for example, sodium diethyldithiocarbonate. A detecting device of this kind can be utilized as a dosimeter in that the impregnated carrier is soaked with the reagent solution and that part of its surface which is exposed to the ambient makes possible access of the copper aerosol to the nitric acid whereupon a color reaction with the indicator takes place which is recognizable from outside by the user.

The advantage of the invention is seen essentially in that the contents of the reagent supply vessel do not pour over the carrier in an uncontrollable manner directly after breaking the reagent supply vessel; instead, the content of the vessel is first held in a collection chamber and from there the content has a uniform and controllable access to the carrier. This ensures that the carrier is wetted uniformly at its surface exposed to the reagent solution so that a further advance of the reagent solution through the porous color indicator carrier is ensured thereafter. In this way, a uniform advance of the color zone along the color indicator carrier is recognizable by the user of a testing tube or, when using a dosimeter, the change of the color intensity over the entire visible carrier region is uniformly distributed so that a comparison with a color standard leads to reliable results.

In the embodiments shown, the reagent vessel and the carrier are disposed along different axes of the housing, with the collection chamber disposed between them.

For measuring with a testing tube, the tube is first opened at both ends but without destroying the reagent supply vessel. Thereafter, the air sample containing the test quantity to be detected is drawn over the carrier. The test quantity enters into a reaction with a reagent impregnated in the carrier with this reaction at first being invisible or, in the simplest case, the test quantity is adsorbed onto the carrier surface. After taking the sample, the reagent supply vessel is destroyed and the reagent solution pours into the reagent collection chamber and is transported in the porous carrier. During the transport, the substance disposed on the carrier surface enters into a color-change reaction with the reagent solution. The advancement of the color zone formed in this manner provides a measure for the test quantity first held on the carrier and can be read off directly as a concentration value with a calibrated testing tube when the test quantity is known. For this purpose, and as is conventional in testing tube measurement technology, a longitudinal scale in ppm (parts per million) is applied on the glass wall of the testing tube along the visible carrier.

An especially advantageous embodiment of the reagent collection chamber comprises configuring this chamber in the form of a siphon-like channel having a volume which can be filled with the reagent up to the level of wetting the end face of the carrier. The channel is bounded at its one end by the reagent supply vessel and at its other end, the channel is bounded by the surface of the carrier exposed to the reagent solution with this surface extending into the collection chamber as an end face. The channel is so configured that it defines a connection for the liquid in the manner of a communicating tube between the reagent supply vessel and the carrier when the supply vessel is opened such that, when the supply vessel is emptied, the liquid level in the reagent collection chamber completely wets the surface of the carrier subjected to the reagent solution because of the static liquid pressure. In this way, and directly after emptying the supply vessel, the reagent solution can be drawn into the porous body of the carrier because of the capillary forces. After the carrier has been saturated with the reagent, then a residual of the reagent liquid can remain in the collection chamber with an appropriate dimensioning of the supply vessel and the channel volume thereby maintaining the liquid connection to the carrier so that the reagent collection chamber maintains a supply of the reagent liquid whereby a desiccation of the carrier exposed to the test quantity is avoided over a longer period of time.

For a uniform wetting of the surface of the carrier extending into the collection chamber, it is advantageous to permit the carrier to extend only slightly into the collection chamber with the remainder thereof being essentially flush with the wall of the collection chamber.

It is advantageous to provide a sponge-like filler in the reagent collection chamber to improve handling characteristics. The liquid drawn thereinto can now be conducted to the surface of the carrier which is to be exposed to the reagent independently of position.

A part of the wall of the reagent collection chamber is configured as a penetrable inlet for the passage of the reagent. This penetrable inlet can be in the form of a self-sealing septum through which a separate syringe filled with the reagent liquid can be pierced with its cannula in order to inject the reagent liquid into the reagent collection chamber or, the inlet can be an additional self-sealing septum mounted on the reagent collection chamber in order to inject an additional reaction component into the already filled reagent collection chamber with the reaction component being required for the course of the color reaction and with this reaction component being injected in addition to the actual reagent liquid. This mixture is generated in the reagent collection chamber and activates the reaction components in the carrier and is taken up by the latter. This is especially advantageous for such cases wherein reaction components not capable of storage are applied directly in advance of the color-change reaction. In both cases, the separate syringe functions as reagent supply vessel.

In addition to the siphon-like channel configuration, the collection chamber can also have a spherically-shaped form which has been shown to be especially advantageous for the arrangement of a self-sealing septum as an inlet for the reagent liquid. Accordingly, only the content of a syringe has to be injected into the reagent collection chamber with the detecting device being held with the collection chamber downwardly so that the supply in the collection chamber is disposed in the hemisphere volume facing away from the carrier. After ending the injection, the detecting device must be rotated only until the liquid content is above the surface of the carrier extending into the collection chamber.

In a further advantageous embodiment of the invention, the supply vessel is accommodated in a receiving holder wherein the supply vessel rests on a thorn-like projection with the supply vessel being destroyed by pressing it into the projection. In this way, the penetrable inlet is formed in the wall of the reagent collection chamber by means of a wall portion of the supply vessel. The thorn-like projection is preferably disposed in the reagent collection chamber so that, when the supply vessel is destroyed, the content of the vessel can immediately pour into the collection chamber. By configuring the supply vessel as a breakable glass ampule, the latter is pushed into the receiving opening of the receiving holder and is pressed against the thorn only when carrying out the detection reaction so that the thorn penetrates the ampule at the base and destroys the same.

An embodiment which is likewise advantageous comprises accommodating the supply vessel for the reagent in a receiving holder which can be pressed inwardly from the outside. For destroying the supply vessel, a wall portion of the receiving holder is configured as being elastic or depressable and is pressed against the supply vessel lying against this wall portion whereby the supply vessel is destroyed. The supply vessel can, for example, be a glass ampule or a plastic bag filled with the reagent liquid.

If a destroyable ampule is used as a supply vessel, then a cap is provided over the ampule with the cap being provided with a depth stop up to which the ampule can be pressed into its receiving holder for destroying the ampule. This provides a reliable handling of the detecting device during the destruction operation. The cap at the same time defines a seal of the receiving holder with respect to the ambient so that, when pressing in the ampule, a pump action is applied to the liquid flowing from the ampule with which the content of the ampule is pressed into the reagent collection chamber.

It is advantageous to provide the cap with closeable vent openings which are closed by the user when pressing in the cap in order to obtain the desired pump action but which are cleared after pressing to make possible a complete emptying of the opened ampule into the collection chamber.

A portion of the carrier surface is exposed to the test quantity to be detected when utilizing the colorimetric detecting device as a dosimeter. The surface of the carrier should not be disadvantageously changed during operational readiness in advance of carrying out a measurement by pollutants of the ambient atmosphere. To achieve this, it is advantageous to cover the carrier in the housing with a protective foil at its surface subjected to the test quantity and showing the color change.

A vent opening is provided in the housing portion receiving the supply vessel in order to facilitate emptying of the destroyed reagent supply vessel. This vent opening is likewise covered with a protective foil. The protective foil is preferably made of one piece and extends over the carrier and the vent opening so that it must simply be pulled off in preparation for a measurement in order that the detecting device be ready for carrying out a measurement.

An especially advantageous embodiment of the colorimetric detecting device is provided by impregnating the carrier with reaction components necessary for the color-change reaction on a substance region facing toward the reagent collection chamber which reaction components, after wetting with the reagent solution, are transportable via capillary forces in the carrier to the surface of the carrier subjected to the test quantity in which a detecting substance is disposed. This detecting substance enters into a color-change reaction with the reaction components and the reagent solution in coaction with the test quantity. With this arrangement, a significant advantage is obtained in that, in the carrier the reaction components necessary for the color-change reaction and a detecting substance, which enters into a color-change reaction with the testing quantity, are each separately stored on opposite ends of the carrier without a reaction occurring so long as the reagent solution does not effect the coming together of all reactants required for the detection via transport within the porous carrier. The separation of the reactants ensures that they cannot react with one another during a more or less long operational readiness time duration. This would make a subsequent detection measurement ineffective; instead, the reactants are each stored chemically stable on the carrier and are brought together in the carrier only for carrying out a measurement with the aid of transport characteristics of the reagent solution and at that location of the carrier which is to be subjected to the test quantity and which can be viewed through the housing. Such a spatial separation of reaction components in the porous carrier is then especially advantageous when the color-change reaction takes place with the aid of an enzyme bound to the carrier as a detecting substance and the reaction components are substrates required for the enzyme for an enzymatic reaction or are substances activating the enzyme or chromogens. The reagent liquid can then either be a buffer solution or a chromogen solution depending on which reaction components are present in the carrier. Enzymatic reactions only take place when the corresponding substrate is brought into reaction contact with the enzyme.

With the separation of enzyme and reaction components (substrate, activator, chromogen, as examples), the condition is prevented that the reaction components react with each other in an undesired manner already during the operational readiness time duration of the detecting device because of high humidity in the ambient.

For the enzymatic detection of, for example, hydrogen peroxide as substrate for the enzyme, horse radish peroxidase, the reagent liquid contains a solution of 1 mMol/l of 4-aminoantipyrin and N-ethyl-N-sulfopropyl-m-toluidine in a 50 mMol/l phosphate buffer. The phosphate buffer should ensure a pH-value of 7.3. With a preparation of this kind, hydrogen peroxide is selectively detectable via the peroxidase (POD) as biocatalyzer by means of a color reaction. In this context, aminoantipyrin and ethyl-sulfopropyltoluidine form the chromogens which combine to a colorant because of the enzyme reaction.

A further example for the application of a carrier with spatially separated reaction components is a dosimeter for the detection of mercaptan. For this purpose, the carrier contains Cu(II)-acetate dissolved in diluted acetic acid and is impregnated with sulfur in the substance region. The reagent supply vessel is filled with m-xylol. If mercaptan is present, then the mercaptan reacts with the Cu(II)-acetate. The m-xylol flows from the destroyed supply vessel and dissolves the sulfur and transports the sulfur to the detecting region where it leads to an increased yellow-brown color reaction in combination with the Cu-(II)-acetate and the mercaptan. The mercaptan indeed forms a light yellow mercaptide compound with Cu-(II)-acetate; however, this mercaptide compound is converted to a more readily recognizable yellow-brown copper compound by means of the transport of the sulfur dissolved in xylol.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
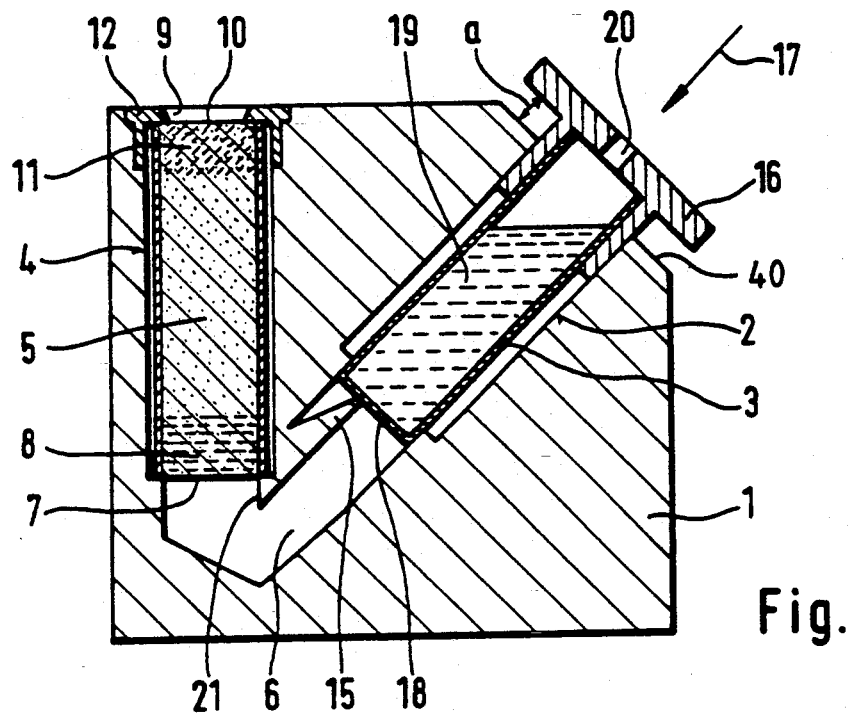
FIG. 1 is a section view of a colorimetric detecting device according to the invention having a reagent supply vessel and a color indicator carrier.

The colorimetric detecting device shown in FIG. 1 has a housing containing a receiving holder 2 for a reagent supply vessel 3 and an insert 4 for accommodating a porous carrier 5. The carrier 5 is held in the carrier insert 4 by a clamping ring 12. The receiving holder 2 and the carrier insert 4 are connected to each other via a siphon-like channel defining a reagent collection chamber 6. The carrier 5 with its end face 7 extends into the reagent collection chamber 6. This end face 7 is subjectable to the reagent. A substance region 8 extends from the end face 7 and is impregnated with the reaction constituents necessary for the color reaction. The reaction constituents can, for example, be chromogens, additional substrates or activators. The impregnation can be realized by freeze drying onto the porous carrier.

The carrier insert 4 has an inlet opening 9 through which the test quantity to be detected has access to the detecting surface 10 of the carrier 5. A color change taking place in the course of the measurement is visible by means of the inlet opening 9. The detecting region 11 follows the detecting surface 10 in the carrier 5 and contains the detecting substances necessary for the color change. For an enzymatic detection, these substances are, for example, the enzymes catalyzing the reaction. In the form illustrated, the particular reactants are spatially separated from each other in the carrier 5 in the substance region 8 and detection region 11, respectively. The reagent supply vessel 3 rests on a thorn-like projection 15 in the receiving holder 2 and is covered with a cap 16 with respect to the housing 1.

The cap 16 can be pressed downwardly a distance (a) up to a depth stop 40 in the direction of arrow 17. When the cap 16 is pressed to the stop 40, the supply vessel 3 is penetrated at its penetrable wall 18 by the thorn 15 so that the reagent liquid pours from the supply vessel 3 through the opening formed in the wall 18 and into the reagent collection chamber 6. While pressing the cap 16 downwardly, a vent opening 20 is held closed so that during pressing in the direction of arrow 17, the reagent liquid 19 is forcibly pushed through the penetrated wall 18 into the collection chamber 6. After releasing the vent opening 20, the residual of the reagent liquid 19 pours from the supply vessel 3 into the collection chamber 6 so that the reagent liquid 19 is brought into contact with the end face 7 of the carrier 5 at the pass-through opening 21 of the collection chamber 6.

The dissolved reaction constituents in the substance region 8 are transported through the carrier 5 up to the detecting region 11 via the capillary forces of the porous carrier 5. The reaction constituents combine with the detecting substance in dissolved form and thereby are suitable for analyzing a test quantity as a substrate for the enzyme. The test quantity can, for example, be an air sample from the ambient which reaches the detecting surface 10 via diffusion or the test quantity can be a liquid which, for example, is applied to the detecting surface via a pipette and thereafter dries onto the carrier.

Figure 2:
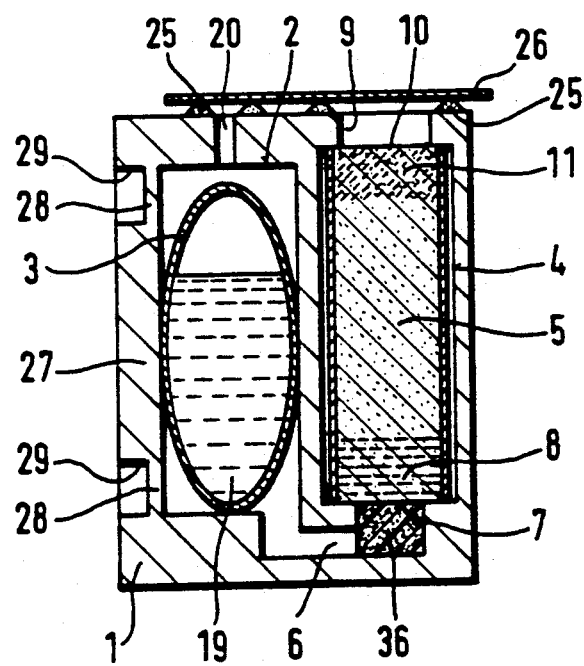
FIG. 2 is a section view of another embodiment of the detecting device of the invention wherein a supply vessel is provided which can be pressed to burst the same; and, FIG. 3 is a section view of still another embodiment of the invention having a supply vessel with a self-sealing septum.

In FIG. 2, the housing 1 contains the carrier 5 in the carrier insert 4 as well as the reagent supply vessel 3 with its reagent liquid 19. The receiving holder 2 for the reagent supply vessel 3 is provided with a vent opening 20 which is closed off by a membrane 26 resting on a self-adhering annular seal 25. This membrane 26 likewise closes the detecting opening 9 and therefore the detecting surface 10 of the carrier 5 in that the membrane 26 is applied to a self-adhering annular seal 25 surrounding the detecting opening 9. The receiving holder 2 can be pressed inwardly at its wall 27 by providing wall regions 28 of reduced thickness which are delimited by corresponding notches 29 in the wall 27. By pressing in the wall 27, the reagent supply vessel 3 is destroyed so that the reagent liquid 19 fills the channel-shaped reagent collection chamber 6 up to the end face 7 of the carrier 5. A portion of the reagent collection chamber 6 is provided with a sponge-like filler 36 in contact with the end face 7. The reagent solution 19 is transported to the detecting surface 10 via capillary forces in the porous carrier 5. The detecting surface 10 is disposed at the detecting opening 9 exposed to the test quantity.

For the detection, the membrane 26 is removed from the detecting opening 9 as well as from the vent opening 20 for the detection so that a follow-up transport of the reagent liquid can take place unhindered in dependence upon its consumption at the detecting surface 10. The reagent supply vessel 3 can then either be configured as a glass ampule or this vessel can comprise a plastic bag filled with the reagent solution 19.

Figure 3:
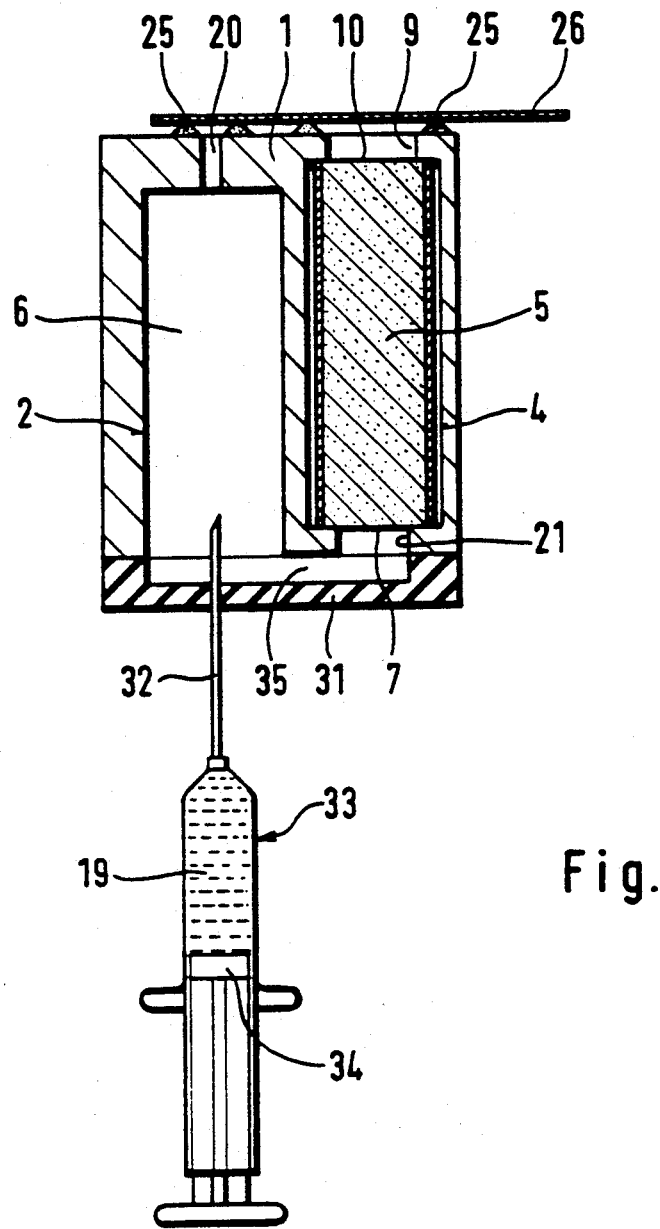

The configuration of the embodiment of FIG. 3 is especially simple since the housing 1 thereof is configured so that the carrier insert 4 for the carrier 5 and the receiving holder 2 are aligned parallel to each other. The receiving holder 2 at the same time defines the reagent collection chamber 6 since the reagent solution 19 is supplied from outside of the housing 1. The reagent collection chamber 6 is provided with a self-sealing septum 31 through which a cannula 32 of a syringe 33 can be pushed with the syringe being filled with the reagent solution 19. The syringe 33 takes over the function of the reagent supply vessel. By displacing the piston 34 of the syringe 33 forwardly, the reagent solution 19 is emptied into the reagent collection chamber 6 from which it can flow over directly through a channel 35 to the end face 7 and wet the latter.

It is understood that the foregoing description is that of the preferred embodiments of the invention and that various changes and modifications may be made thereto without departing from the spirit and scope of the invention as defined in the appended claims.

What is claimed is:

1. A colorimetric detecting device for detecting a gaseous test quantity, the detecting device comprising:

a housing having a first recess having a first longitudinal axis formed therein and an unobstructed clear opening communicating with said first recess to permit the gaseous test quantity to migrate to said first recess;

a carrier having first and second end faces and at least one side wall perpendicular to said first and second end faces, said carrier being seated in said first recess, and said first end face being disposed at said opening so as to be directly viewable by an observer through said opening;

said first end face defining an unobstructed detecting surface exposed directly to the gaseous test quantity to be detected and have a detecting region below said detecting surface;

said housing having a second recess having a second longitudinal axis different from said first axis formed therein;

a reagent supply vessel seated in said second recess and containing a reagent solution;

said second end face being disposed opposite said first end face;

said carrier having a substance region in said carrier in the vicinity of said second end face containing a reaction constituent having a color indicator;

said reaction constituent having said color indicator being impregnated in said substance region of said carrier;

said detecting region containing a detecting substance and being in spaced relationship to said substance region within said carrier;

releasing means mounted on said housing for acting on said vessel to permit said reagent solution to pour out of said vessel;

said housing defining a reagent chamber formed therein between said second recess and said second end face for receiving said reagent solution released from said vessel and allowing said reagent solution to come into contact with said second end face of said carrier for uniformly wetting said second end face and for dissolving said reaction constituent thereby preventing said reagent solution from pouring over said carrier in an uncontrolled manner; and, said carrier being a porous body to facilitate a capillary movement up to said detecting region by said reagent solution with said dissolved reaction constituent therein to combine with said detecting substance and said gaseous test quantity to form a reaction product which enters into a color-changing reaction with said color indicator to provide a color change on said detecting surface directly viewable by an observer through said opening.

2. The colorimetric detecting device of claim 1, said reagent collection chamber being formed in said housing so as to define a channel defining a siphon and extending between said carrier and said vessel; and, said channel having a volume less than the volume of said vessel so as to become filled with said reagent solution to the extend required to wet said second end face when said reagent solution is released from said vessel and to saturate the carrier to ensure said capillary movement.

3. The colorimetric detecting device of claim 1, said housing having an interior housing wall and a depressable outside wall delimiting said second recess; and, said releasing means including said depressable outside wall for permitting a user to press said vessel against said interior wall to rupture said vessel to permit said reagent solution to flow from said vessel into said chamber.

4. The colorimetric detecting device of claim 1, said releasing means including a sharp projection formed in said second recess; and, said supply vessel being mounted in said second recess so as to be pressable against said projection for destroying said vessel to permit said reagent solution to pour into said chamber.

5. The colorimetric detecting device of claim 4, said releasing means including means for pressing said vessel against said projection from outside of said housing.

6. The colorimetric detecting device of claim 5, said means for pressing said vessel being a cap mounted on said vessel and in said second recess so as to be movable between first and second positions on said housing to push said vessel against said projection as said cap is moved into said second position; and, stop means formed on said housing to define said second position.

7. The colorimetric detecting device of claim 6, said release means further including a vent opening formed in said cap and adapted to be closeable when pushing said cap from said first position to said second position.

8. The colorimetric detecting device of claim 7, said device further comprising a protective foil to cover said opening formed in said housing and said vent opening.

9. The colorimetric detecting device of claim 1, said device further comprising a protective foil to cover said opening during non-use of said device to protect said detecting surface of said carrier from pollutants in the ambient.

10. The colorimetric detecting device of claim 1, said detecting substance being an enzyme bound to said porous body in said detecting region; said reaction constituent being required for an enzymatic reaction with the test quantity; and, said color indicator being a chromogen reagent.

11. The colorimetric detecting device of claim 1, said detecting substance being an enzyme bound to said carrier in said detecting region; said reaction constituent in said substance region being at least one substrate and said color indicator being at least one chromogen; and, said reagent solution being an aqueous buffer solution.

12. The colorimetric detecting device of claim 1, said device further comprising a porous filler disposed in said reagent collection chamber.

13. The colorimetric detecting device of claim 1, said vessel being a destroyable ampule.

14. The colorimetric detecting device of claim 1, said carrier being mounted in said housing so as to cause only said second end face thereof to face into said reagent chamber.

15. A colorimetric detecting device for a gaseous test quantity, the detecting device comprising:

a housing having a first recess having a first longitudinal axis formed therein and an unobstructed clear opening communicating with said first recess to permit the gaseous test quantity to migrate to said first recess;

a carrier having first and second end faces and at least one side wall perpendicular to said first and second end faces, said carrier being seated in said first recess, and said first end face being disposed at said opening so as to be directly viewable by an observer through said opening;

said first end face defining an unobstructed detecting surface exposed directly to the gaseous test quantity to be detected and having a detecting region below said detecting surface;

a detecting substance disposed in said carrier;

said housing having a second recess having a second longitudinal axis different from said first axis formed therein;

a reagent supply vessel seated in said second recess and containing a reagent solution having a reaction constituent dissolved therein;

said reaction constituent containing a color indicator;

said second end face being disposed opposite said first end face;

releasing means mounted on said housing for acting on said vessel to permit said reagent solution to pour out of said vessel;

said housing defining a reagent chamber formed therein between said second recess and said second end face for receiving said reagent solution released from said vessel and allowing said reagent solution to come into contact with said second end face of said carrier for uniformly wetting said second end face thereby preventing said reagent solution from pouring over said carrier in an uncontrolled manner; and, said carrier being a porous body to facilitate a capillary movement up to said detecting region by said reagent solution to combine with said detecting substance and said gaseous test quantity to form a reaction product which enters into a reaction with said color indicator to provide a color change on said detecting surface directly viewable by an observer through said opening.

16. The colorimetric detecting device of claim 15, said carrier being mounted in said housing so as to cause only said second end face thereof to face into said reagent collection chamber thereby preventing said reagent solution from pouring over said carrier in an uncontrolled manner.

17. The colorimetric detecting device of claim 15, said reagent collection chamber being formed in said housing so as to define a channel defining a siphon and extending between said carrier and said vessel; and, said channel having a volume less than the volume of said vessel so as to become filled with said reagent solution to the extent required to wet said second end face when said reagent solution is released from said vessel and to saturate the carrier to ensure said capillary movement.

18. The colorimetric detecting device of claim 15, said housing having an interior housing wall and a depressable outside wall delimiting said second recess; and, said releasing means including said depressable outside wall for permitting a user to press said vessel against said interior wall to rupture said vessel to permit said reagent solution to flow from said vessel into said chamber.

19. The colorimetric detecting device of claim 15, said releasing means including a sharp projection formed in said second recess; and, said supply vessel being mounted in said second recess so as to be pressable against said projection for destroying said vessel to permit said reagent solution to pour into said chamber.

20. The colorimetric detecting device of claim 19, said releasing means including means for pressing said vessel against said projection from outside of said housing.

21. The colorimetric detecting device of claim 20, said means for pressing said vessel being a cap mounted on said vessel and in said second recess so as to be movable between first and second positions on said housing to push said vessel against said projection as said cap is moved into said second position; and, stop means formed on said housing to define said second position.

22. The colorimetric detecting device of claim 21, said release means further including a vent opening formed in said cap and adapted to be closeable when pushing said cap from said first position to said second position.

23. The colorimetric detecting device of claim 22, said device further comprising a protective foil to cover said opening formed in said housing and said vent opening.

24. The colorimetric detecting device of claim 15, said detecting substance being an enzyme bound to said porous body in said detecting region; said reaction constituent being required for an enzymatic reaction with the test quantity; and, said color indicator being a chromogen reagent.

25. The colorimetric detecting device of claim 15, said detecting substance being an enzyme bound to said carrier in said detecting region; said reaction constituent in said substance region being at least one substrate and said color indicator being of at least one chromogen; and, said reagent solution being an aqueous buffer solution.

26. The colorimetric detecting device of claim 15, said vessel being a destroyable ampule.

27. A colorimetric detecting kit for a gaseous test quantity, the detecting kit comprising:

a housing having a first recess having a first longitudinal axis formed therein and an unobstructed clear opening communicating with said first recess to permit the gaseous test quantity to migrate to said first recess;

a carrier having first and second end faces and at least one side wall perpendicular to said first and second end faces, said carrier being seated in said first recess and having a first end face being disposed at said opening so as to be directly viewable by an observer through said opening;

said first end face defining an unobstructed detecting surface exposed directly to the gaseous test quantity to be detected and having a detecting region below said detecting surface;

said housing having a second recess having a second longitudinal axis different from said first axis formed therein;

said second end face being disposed opposite said first end face;

said carrier having a substance region in said carrier in the vicinity of said second end face containing a reaction constituent having a color indicator;

said detecting region being in spaced relationship to said substance region within said carrier;

said housing having a wall in the form of a self-sealing septum delimiting said second recess;

said housing defining a channel formed therein between said second recess and said second end face for conducting a reagent solution to said second end face of said carrier for uniformly wetting said second end face and for dissolving said reaction constituent thereby preventing said reagent solution from pouring over said carrier in an uncontrolled manner;

said carrier being a porous body to facilitate a capillary movement up to said detecting region by said reagent solution with said dissolved reaction constituent therein to combine with said detecting substance and said gaseous test quantity to form a reaction product which enters into a color-changing reaction with said color indicator to provide a color change on said detecting surface directly viewable by an observer through said opening; and, a manually actuable reagent supply vessel containing said reagent solution, said vessel being separate from said housing;

said reagent supply vessel being a syringe having a cannula for penetrating said septum to permit said reagent solution to be injected into said second recess.

28. The colorimetric detecting device of claim 27, said carrier being mounted in said housing so as to cause only said second end face thereof to face into said channel.

* * * * *

UNITED STATES PATENT AND TRADEMARK OFFICE
CERTIFICATE OF CORRECTION

PATENT NO. : 5,312,593

DATED : May 17, 1994

INVENTOR(S) : Horst Rabenecker, Klaus-Peter Rindt,
Stephan Scholtissek and Wolfgang Breithaupt It is certified that error appears in the above-identified patent and that said Letters Patent is hereby corrected as shown below:

In column 8, line 32: delete "have" and substitute -- having -- therefor.

In column 9, line 10: delete "extend" and substitute -- extent -- therefor.

Signed and Sealed this

Sixteenth Day of August, 1994

Attest:

BRUCE LEHMAN

*Attesting Officer*  *Commissioner of Patents and Trademarks*